United States Patent [19]
Austin, Jr. et al.

[11] Patent Number: 5,407,565
[45] Date of Patent: Apr. 18, 1995

[54] SOLIDS COLLECTOR USED IN DENTISTRY

[75] Inventors: George K. Austin, Jr., Newberg; David L. Curtis, Tigard, both of Oreg.

[73] Assignee: A-Dec, Inc., Newberg, Oreg.

[21] Appl. No.: 17,425

[22] Filed: Feb. 12, 1993

[51] Int. Cl.⁶ .................. B01D 29/11; A61C 17/08
[52] U.S. Cl. ........................... 210/188; 210/232; 210/406; 210/416.1; 210/435; 210/456; 96/189; 96/197; 433/92; 433/97
[58] Field of Search .............. 210/456, 416.1, 406, 210/435, 232, 188; 433/92, 97; 96/197, 189

[56] References Cited

U.S. PATENT DOCUMENTS

| | | | |
|---|---|---|---|
| 139,645 | 6/1873 | Adney | 210/456 |
| 1,207,625 | 12/1916 | Ritchey | 210/456 |
| 2,627,937 | 2/1953 | Martinet | 183/37 |
| 2,784,717 | 3/1957 | Thompson | 128/276 |
| 2,821,021 | 1/1958 | Winter | 32/33 |
| 3,012,323 | 12/1961 | Thompson | 32/33 |
| 3,138,873 | 6/1964 | Bishop | 32/33 |
| 3,720,316 | 3/1973 | Riesbeck et al. | 210/456 |
| 3,771,226 | 11/1973 | Lieb et al. | 32/22 |
| 3,789,990 | 2/1974 | Drori . | |
| 3,863,635 | 2/1975 | Swatman . | |
| 3,890,712 | 6/1975 | Lopez | 32/33 |
| 3,900,401 | 8/1975 | Oliver et al. . | |
| 4,245,989 | 1/1981 | Folkenroth et al. . | |
| 4,957,629 | 9/1990 | Smith | 210/456 |
| 5,015,184 | 5/1991 | Perry et al. | 433/93 |
| 5,078,603 | 1/1992 | Cohen | 433/91 |
| 5,192,439 | 3/1993 | Roth et al. | 210/456 |

FOREIGN PATENT DOCUMENTS

| | | | |
|---|---|---|---|
| 846654 | 6/1952 | Germany | 210/456 |
| 2459881 | 6/1976 | Germany . | |
| 2713320 | 9/1978 | Germany . | |
| 910348 | 11/1962 | United Kingdom | 210/456 |
| 1466805 | 3/1977 | United Kingdom . | |

OTHER PUBLICATIONS

A-Dec 117-page equipment catalog, cover and pp. 107, 108, 110, Jan. 1991.
KaVo "Estetica ™ 1042 Ein Wichtiger Schritt in die Zukunft" German language 13-page brochure, p. 6, circa Jan. 1991.
A-Dec 121-page catlaog, cover and pp. 109, 112, circa Sep. 1991.
Marus Dental Equipment 15-page catalog, cover and p. 30, Mar. 1982.
Siemens 27-page catalog, cover and pp. 8-9, Feb. 1991.

*Primary Examiner*—Wilbur Bascomb, Jr.
*Attorney, Agent, or Firm*—Klarquist, Sparkman Campbell Leigh & Whinston

[57] ABSTRACT

The solids collector collects solids that may be ejected by an HVE. The collector includes a deflector for efficiently filling the collector.

25 Claims, 3 Drawing Sheets

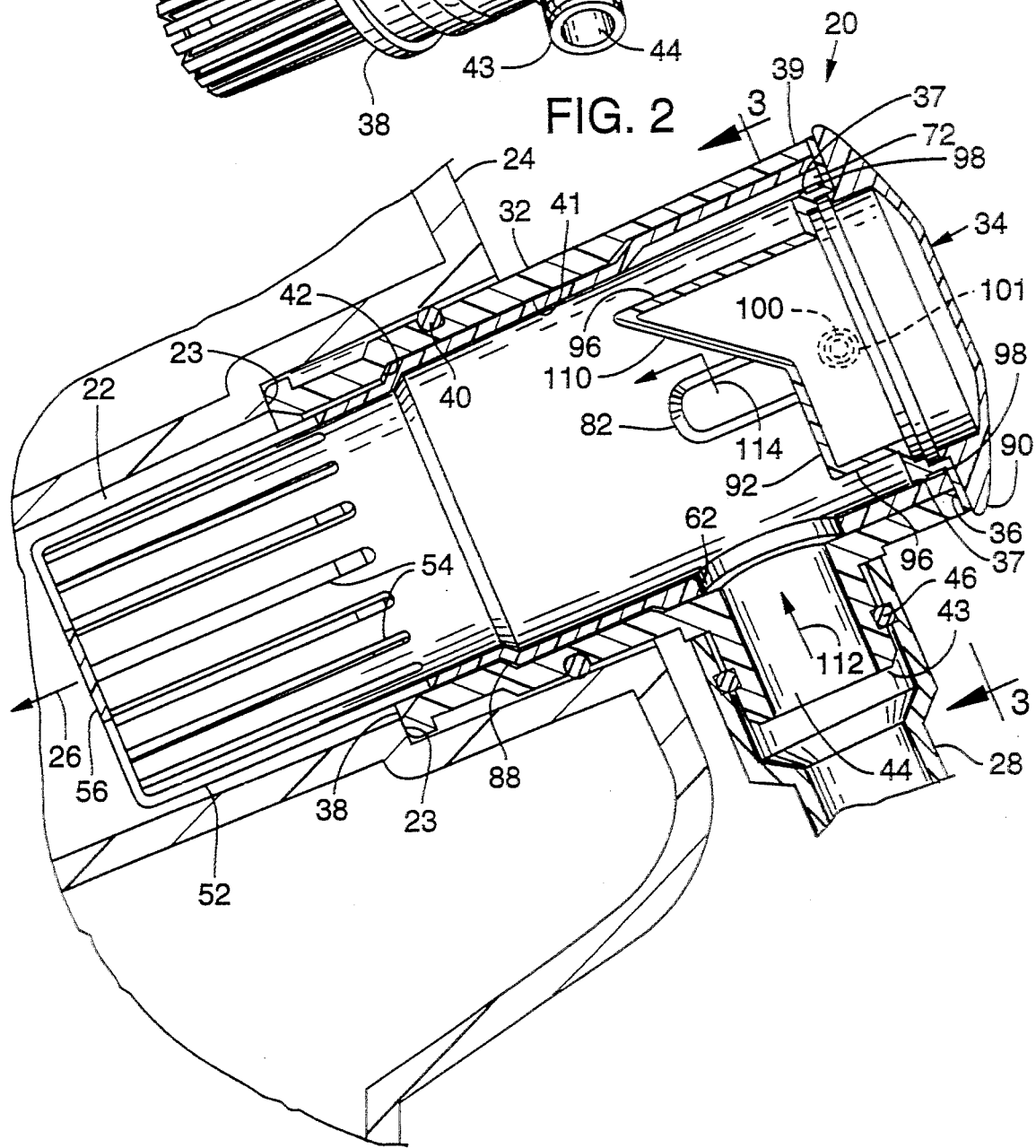

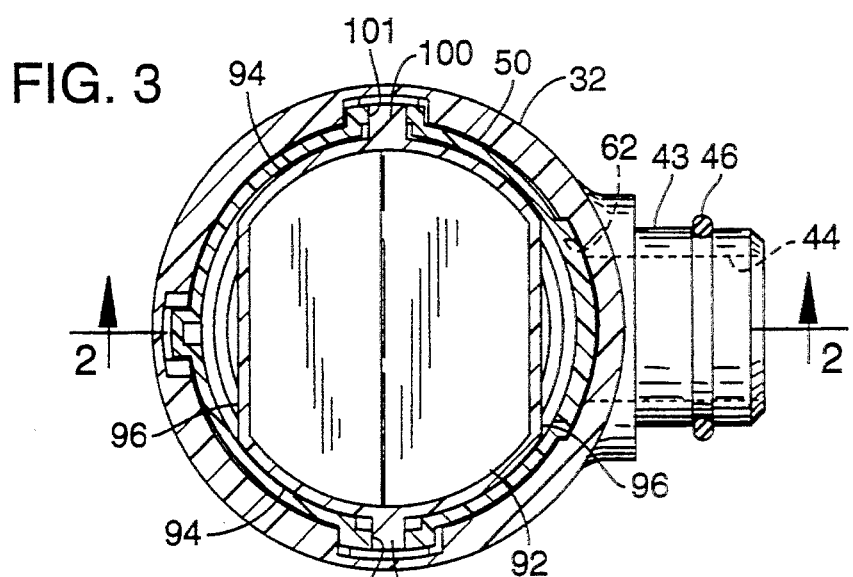
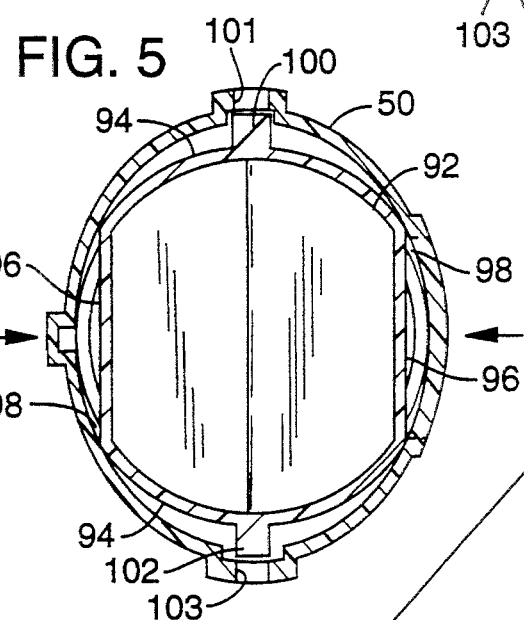
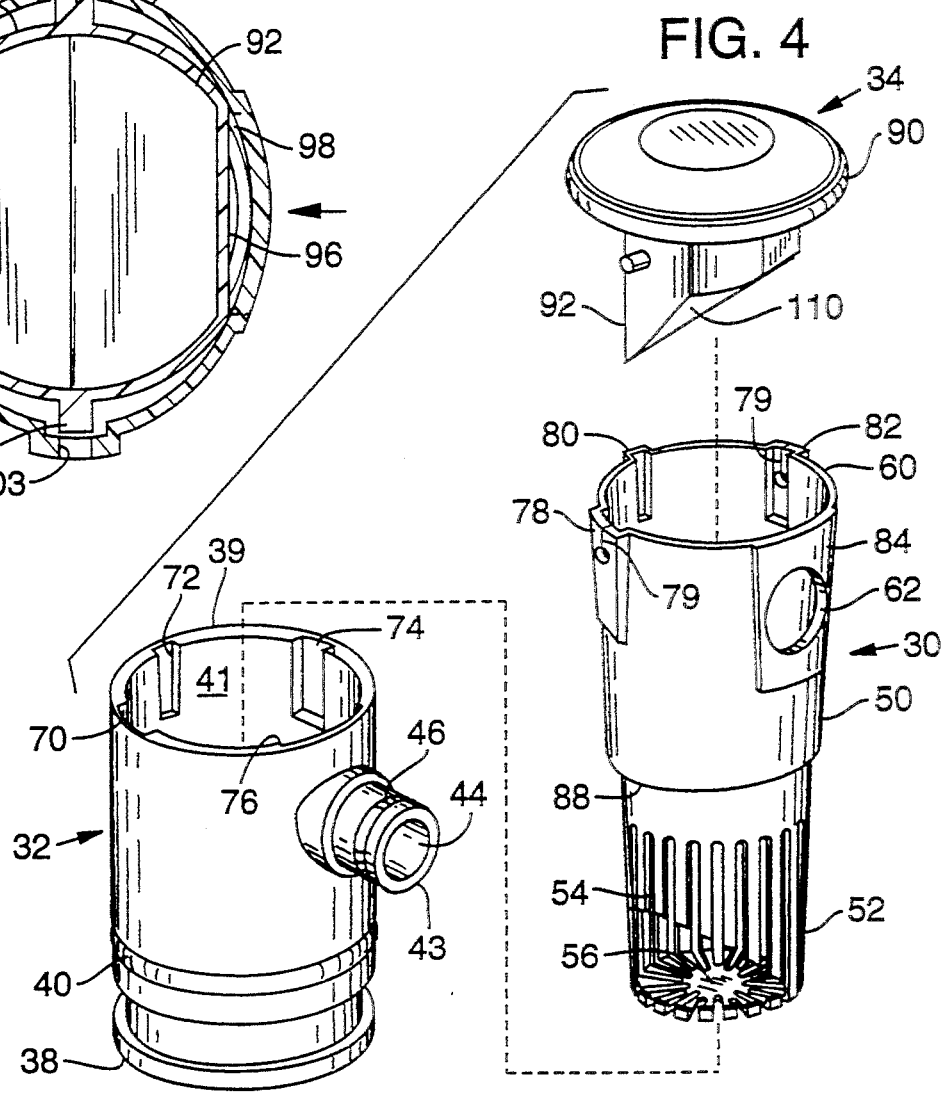

SOLIDS COLLECTOR USED IN DENTISTRY

TECHNICAL FIELD

This invention pertains to mechanisms for collecting solids that are present in fluids that are ejected by high-vacuum evacuation systems used in dentistry.

BACKGROUND INFORMATION

A high-vacuum evacuation systems (commonly referred to as an HVE) is activated by the dentist or assistant to remove from a patient's mouth loose particles that may be generated during dental procedures. For example, solid particles, such as those generated as a result of drilling, are drawn into the HVE. A typical HVE includes a tube, to one end of which is attached a tip that fits inside a dental patient's mouth. The other end of the tube is connected to a suction pump.

A solids collector generally comprises a screen, trap or other mechanism for collecting the ejected solid particles. The collector is connected between the HVE tip and the suction pump to prevent large particles from entering the vacuum system, which may cause damage or clogging. The collector also serves to trap a crown or bridge that may be accidentally evacuated.

The accumulation of solids in the solids collector requires the periodic emptying or replacement of the collector. Emptying or replacing the collector, in addition to being time consuming, requires careful handling followed by handwashing.

SUMMARY OF THE INVENTION

This invention is directed to a solids collector that is used with an HVE and designed so that the volume available for collecting evacuated solids is fully and compactly filled during use of the HVE, thereby minimizing the frequency with which the collector must be emptied or replaced.

The solids collector generally comprises a hollow collector member that is defined by a cylindrical body having a side wall and opposing ends. One end of the collector member carries a strainer. The collector member is connectable to a suction source so that fluid entering the collector member is drawn through the strainer, the strainer trapping solid particles for later disposal.

The collector member has an inlet opening formed in its side wall. Fluid from the HVE enters the collector member through the inlet opening. A cap is attached to the end of the collector member that is opposite that of the strainer. Preferably, the collector member and cap are easily detached from one another so that a filled collector member may be easily disposed of and replaced.

The cap includes a deflector that protrudes into the path of the fluid that flows into the collector member from the HVE. The deflector serves to redirect that flow toward the bottom of the strainer. As a result, the strainer fills efficiently from bottom to top, and solids do not accumulate against the side wall of the collector member. In the absence of a deflector, such accumulation would tend to clog the inlet opening of the collector member before the strainer is completely filled. The effect of the deflector in directing the solids toward the strainer (that is, away from the cap) reduces the likelihood of solids material accumulating in the vicinity where the cap detaches from the collector member, hence reducing the likelihood that solids will spill from the collector member when the cap is detached.

BRIEF DESCRIPTION OF THE DRAWINGS

FIG. 1 is a perspective view of a solids collector formed in accordance with the present invention.

FIG. 2 is a longitudinal cross-sectional view of the solids collector taken along line 2—2 of FIG. 3 and showing the collector installed within a receptacle in a control panel.

FIG. 3 is a cross-sectional view of the capped end of the collector taken along line 3—3 in FIG. 2.

FIG. 4 is an exploded, perspective view of the collector.

FIG. 5 is a sectional view of part of the collector taken along line 3—3 of FIG. 2 and depicting the technique for detaching the cap from the body of the collector member.

DETAILED DESCRIPTION OF PREFERRED EMBODIMENTS

Figure 6:
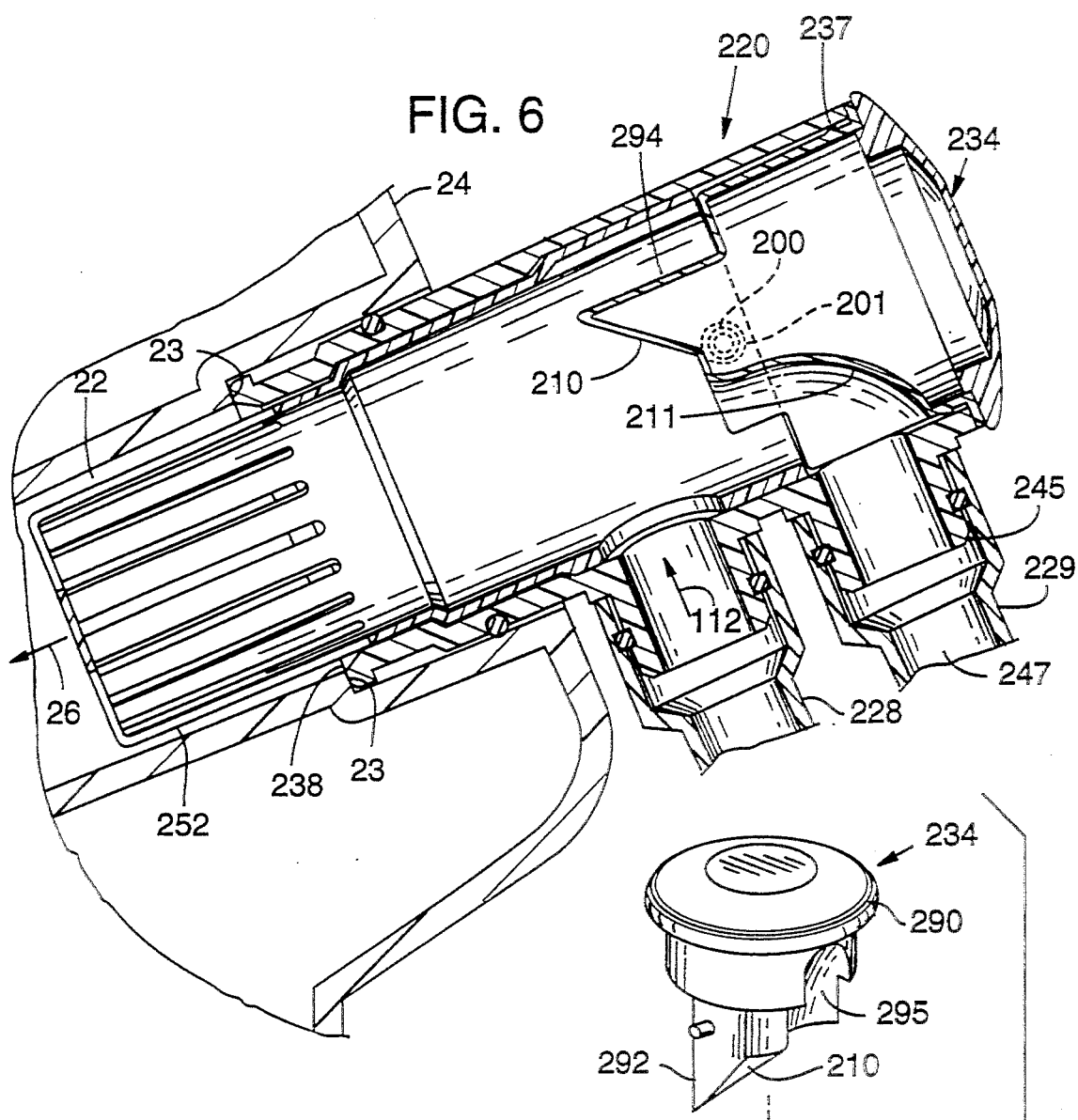
FIG. 6 is a longitudinal cross-sectional view of an alternative embodiment of a collector that is constructed such that a second component, such as a saliva ejector, may be connected thereto for directing a second stream of ejected fluids through the strainer.

With reference to FIGS. 1 and 2, the solids collector 20 of the present invention is connected between a suction source and an HVE. Specifically, the generally cylindrical collector 20 is installed in a correspondingly shaped receptacle 22 formed in a control panel 24 or similar component in the vicinity of a dental patient. A conventional suction source, such as a pump, may be activated by the dentist or assistant for applying suction to the receptacle in a direction represented by arrow 26 (FIG. 2).

A tube 28 is connected at one end to the installed solids collector 20, the other end of the tube carrying the tip of a conventional HVE (not shown). The suction that is applied to the receptacle is communicated through a strainer 52 portion of the collector and through the attached tube 28. As a result, saliva, water, and solid particles, such as those generated as a result of drilling, are drawn through the HVE and the collector. Solids having a minimum dimension greater than about 1 mm become trapped in the strainer of the solids collector for disposal as described below.

With reference to FIGS. 1, 2 and 4, the solids collector 20 includes three primary components, including a collector member 30, a connector 32, and a cap 34. The connector 32 is a hollow, generally cylindrical member, into which fits the collector member 30. More particularly, the connector 32 is made of injection-molded plastic, and fits snugly within the correspondingly shaped receptacle 22. The inner end 38 of the connector that is inserted into the receptacle slides inwardly until that end 38 contacts an annular rim 23 that is formed by the wall of the receptacle (FIG. 2).

Near the inner end 38 of the connector 32 a circumferential exterior groove is formed, into which is tightly fit an O ring 40. The O ring 40 seals the narrow annular space between the connector 32 and the interior wall of the receptacle 22.

Between the O ring 40 and the inner end 38 of the connector 32, the diameter of the connector is reduced slightly to define an inclined annular shoulder 42 in the interior surface 41 of the connector. The shoulder 42 serves to seat the strainer end of the collector member 30 and to center the strainer within the receptacle. The interior surface 41 of the connector 32 is shaped to define a gradually increasing internal diameter of the connector from the shoulder 42 to the outer end 39 of the connector.

A tubular coupler 43 is formed in the wall of the connector 32. The coupler carries an O ring 46 within a groove on its outer surface. The illustrated end of the HVE tube 28 has a corresponding internal groove that receives the O ring 46 so that the tube 28 fits securely to the coupler 43 to provide fluid communication between the HVE tube and the bore 44 of the coupler 43.

The collector member 30 is also formed of injection-molded plastic and includes a cylindrical body 50, the overall diameter of which is slightly tapered to correspond to the internal diameter of the connector 32 into which the collector member fits.

One end of the body 50 terminates in the integrally formed strainer 52. The strainer 52 is formed by several parallel slots 54 that extend through the side wall of the body 50 along the lower portion (FIG. 4) of that body. The slots 54 continue across part of the bottom wall 56 of the collector member body 50 as best shown in FIG. 4. It is contemplated that any of a multitude of other strainer configurations (for example, perforations) may be employed.

Near the upper edge 60 of the collector member 30, a circular inlet opening 62 is formed completely through the side wall of the body 50. Whenever the collector member 30 is inserted into the connector 32, this inlet opening 62 is axially aligned with the bore 44 of the coupler 43 thereby permitting fluid communication through the opening 62 and the HVE tube 28 that is connected to the coupler 43.

In a preferred embodiment, the collector member 30 and connector 32 are constructed so that whenever the collector member is fit into the connector, the inlet opening 62 will be in axial alignment with the coupler bore 44. To this end, recessed keyways 70, 72, 74, 76 are formed in the internal surface 41 of the connector 32, which keyways mate with keys 78, 80, 82, 84 that are formed to protrude from the outer surface of the collector member body 50. The keyways 70, 72, 74, 76 are formed in the interior wall 41 of the connector 32 to extend inwardly from the outer end 39 of the connector. Preferably, each keyway has a width that is unequal to the width of any other keyway. Similarly, each key 78, 80, 82, 84 has a unique width so that one key will fit within only one keyway. As a result, the collector member will fit into the connector 32 only when the keys and keyways correspond such that the inlet opening 62 of the collector member is axially aligned with the bore 44 of the coupler on the connector.

Near the location where the strainer 52 joins the remaining portion of the collector member body 50, the diameter of the body 50 is increased to define an inclined exterior shoulder 88. The shoulder 88 abuts the internal shoulder 42 formed in the wall 41 of the connector 32 whenever the collector member 30 is inserted into the connector 32. When the collector member 30 is properly inserted, substantially all of the strainer 52 protrudes from the inner end 38 of the connector 32, centered within the receptacle 22 (FIG. 2).

The cap 34 of the collector member includes a disk shaped part or lid 90. The overall diameter of the lid 90 is slightly greater than the diameter of the outer end 39 of the connector 32. An integrally attached deflector member 92 protrudes from the underside of the cap. Referring to FIGS. 2 through 5, the deflector member 92 is hollow, and generally oblong shaped in cross-section, having opposing curved side wall portions 94 formed along a diameter that is slightly less than the internal diameter of the upper edge 60 of the collector member body 50 into which the deflector protrudes. The curved side wall portions 94 of the deflector are interrupted by opposing parallel flats 96. The distance between the flats 96 is such that a gap 98 (see FIG. 2) normally resides between each flat 96 and the interior surface of the upper edge 60 of the collector member body 50. The gap provides for the attachment and detachment of the cap, as described next.

With particular reference to FIGS. 4 and 5, each curved side wall portion 94 of the deflector 92 includes an outwardly protruding boss 100, 102. Each boss is a generally cylindrical member integrally formed with the deflector 92. One boss 100 has a diameter (FIG. 3) that is slightly greater than the diameter of the opposing boss 102. When the cap is attached to the collector member body 50, the protruding portion of boss 100 fits within a correspondingly sized hole 101 formed through side wall of the collector member body 50. The opposing boss 102 fits within a correspondingly sized hole 103 formed in the opposing side wall of the collector member body 50.

The depth of the holes 101, 103 (that is, as measured from the upper edge 60 of the body 50) is such that when the cap is attached (that is, when the bosses 100, 102 mate with their corresponding holes 101, 103), the peripheral undersurface 36 of the lid 90 fits tightly against the upper edge 60 of the collector member.

Spaced from the undersurface 36 of the cap is a triangular shaped (in cross section) peripheral protrusion 37 that is pinched, slightly, between the curved side wall portions 94 and the inside wall of the collector member 30 when the cap is attached. The pinched protrusion helps seal the space between the attached cap and collector member.

As best seen in FIG. 2, the deflector 92 is shaped to include an inclined outer surface 110 that faces the inlet opening 62 of the collector member whenever the cap 34 is attached to the body 50. In this regard, it is noteworthy that because of the just-described differences in the diameters of the bosses 100, 102, the cap can be attached to the collector member in no other way than with the inclined surface 110 facing the inlet opening 62.

Fluid, which includes solid particles, in tube 28 is drawn into the collector member 30 as suction is applied to the receptacle 22. Fluid enters the collector member 30 along a path that is represented by arrow 112 (through inlet opening 62) and impinges upon the deflector surface 110 (FIG. 2). The deflector surface is, preferably, inclined 45° relative to the path 112. As a result, the fluid path is redirected as shown at arrow 114 in manner such that the solid particles that are carried in the fluid ejected by the HVE will be deflected directly toward the strainer 52 of the collector member.

As a consequence of the hollow construction of the deflector 92, the surface 110 against which the particles impinge is defined by a thin wall that flexes slightly in response to the impact of the particles. The effect of this flexing is to absorb much of the energy in the moving particles, so that the particles are deflected with significantly reduced velocity compared to the velocity of the particles upon entering the collector. The slowed particles are, therefore, more likely to be re-directed by the deflector toward the bottom wall of the strainer, and less likely to pack in the strainer. Put another way, the deflection and energy absorption of the deflector results in an easy-to-empty, granular collection of particles in the filled strainer.

Preferably, the inclined surface 110 is spaced away from the inlet opening 62. In the preferred embodiment (FIG. 2), the inclined surface is spaced so that fluid flowing through the inlet opening 62 is unaffected by the deflector until the fluid is at least about half-way across the diameter of the collector member body 50. This spaced relationship of the inclined surface 110 and opening 62 prevents solid particles from being deflected directly back toward the opening 62 and adjacent side wall portion of the body, which might otherwise occur if the surface 110 were too close to the opening 62.

The solids collector in the present invention provides, as just described, for efficient filling of the strainer 52 of the collector member because the material entering the collector member is deflected in a way that gradually fills the strainer from its bottom wall 56 toward the top edge 60 of the collector member. Moreover, the deflection provided by flexible surface 110 minimizes the likelihood that solid material will accumulate near the detachable cap, which accumulation may lead to spilling in the event that a filled collector member is not carefully handled when it is replaced.

To replace a filled collector member 30, the dentist or assistant pulls the capped end of the collector member 30 so that collector member slides out of the connector 32. The sides of the collector member body 50 nearest the flats 96 on the deflector 92 are then squeezed together as shown by the arrows in FIG. 5. Those squeezed portions of the collector member body move into the previously mentioned gaps 98, thereby allowing the collector member body 50 to deform in a manner such that the bosses 100 and 102 are disengaged from their associated holes 101, 103. The thus detached collector member can be discarded or emptied.

A new or emptied collector member is attached to the cap by squeezing the opposing sides of the collector member body as depicted by the arrows in FIG. 5, and then inserting the cap into the collector member body until the bosses 100, 102 are aligned with their corresponding holes 101, 103. The collector body is then released so that those bosses move into the holes to attach the cap to the body 50.

In a preferred embodiment, the body 50 of the collector member 30 includes a slit 79 (FIG. 4) between each hole 101, 103 and the top edge 60. That normally-closed slit 79 widens as the collector member sides are squeezed as just described. The widened slit, therefore, provides a path through which an associated boss 100, 102 may move as the cap and body are detached. The widened slits 79 eliminate the need for squeezing the body by such an extent that the bosses must fit completely inside the body before the cap can be detached.

Figure 7:
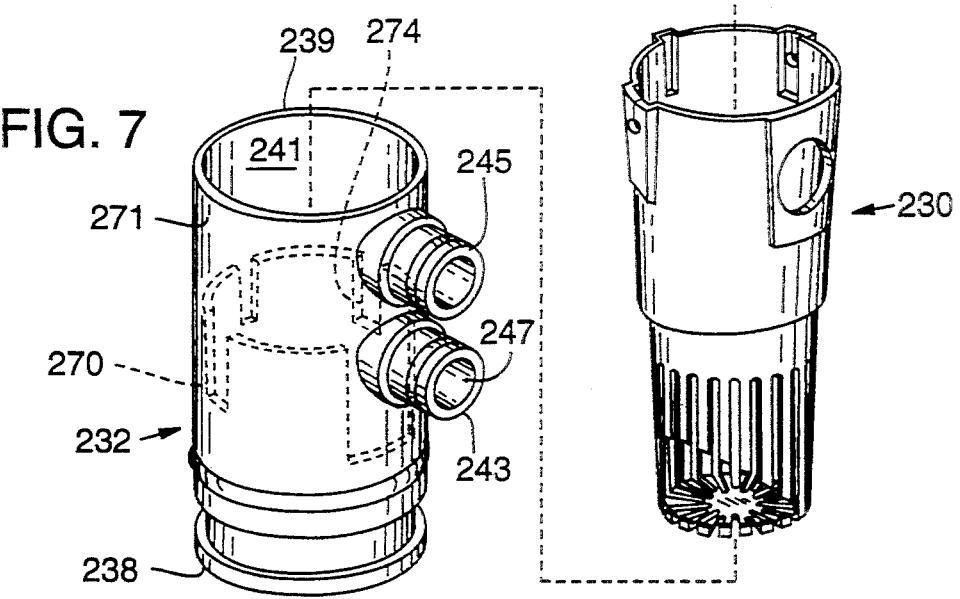
FIG. 7 is an exploded perspective view of the alternative solids collector of FIG. 6.

In another preferred, alternative embodiment (FIGS. 6 and 7), the collector 220 is modified to accommodate, in addition to an HVE tube 228, a second component, such as a saliva ejector. This accommodation is made by modifications to the previously described connector 32 and cap 34 as will be described with reference to FIGS. 6 and 7.

In the alternative embodiment of the solids collector 220, the overall length between the inner end 238 and outer end 239 of the connector 232 is extended as compared to the prior-described embodiment. Specifically, the connector 232 includes a generally cylindrical extension portion 271 generally above (FIG. 7) the coupler 243. The coupler 243 generally conforms to the previously described coupler 43. The internal diameter of the extension piece 271 generally matches the diameter of the surface 241 of the collector member as measured between two keys 270, 274.

The extension portion 271 includes a second tubular coupler 245 formed in the sidewall of the connector 232 in vertical alignment with the first coupler 243. The second coupler 245 includes an exterior groove and O-ring for providing connection with a second-component tube 229 in a manner similar to the coupling technique described in the previously mentioned embodiment.

The cap 234 of the alternative collector 230 is similar to the foregoing described cap 34, except that the region of the cap beneath the protrusion 237 is extended vertically (FIG. 7) by an amount corresponding to the vertical distance provided by the vertical extension 271 of the connector 232. Moreover, only one side of the deflector member 292 includes a flat 294. The opposing side (that is, the side of the deflector member facing the bore 247 of the second coupler 245) is configured to have a smoothly rounded channel 295 formed therein for directing downwardly toward the strainer 252 fluid that enters the collector 232 along the path defined by the bore of the second tube 229.

The depth of the groove 295 (that is, in the direction toward the long center of the solids collector 230) gradually increases in the direction toward the strainer 252, thereby defining an inclined surface 211 for directing the fluid and solids entering the collector 220 through the second coupler. This outer surface 211 is defined, as is the inclined, flat surface 210 beneath it, by a thin wall of the deflector 292 as a consequence of the hollow nature of the deflector. The energy-absorbing characteristics explained in connection with previously described embodiment are, therefore, present in the alternative embodiment.

While the present invention has been described in accordance with preferred embodiments, it is to be understood that substitutions and alterations may be made thereto without departing from the spirit and scope of the appended claims.

The invention claimed is:

1. A solids collector apparatus for use in dentistry, comprising:

a collector member defined by a cylindrical side wall and opposing ends and having a strainer located at one of the ends so that fluid that carries solid particles may be drawn into the collector member by suction applied to the strainer end of the collector member, the collector member having an inlet opening formed in the side wall and through which opening the fluid is drawn into the collector member by the suction;

a deflector attached to the collector member for directing toward the strainer fluid that is drawn into the inlet opening; and a connector into which fits the collector member for connecting the collector member in fluid communication with a suction source, the connector having a coupler attached thereto for connecting a tube to the connector.

2. The apparatus of claim 1 wherein the fluid flows in a first direction as the fluid is drawn into the opening, and wherein the deflector is located to change that first direction of fluid flow to a second direction toward the strainer.

3. The apparatus of claim 1 wherein the deflector is defined by a cap that is removably attached at the collector member end that is opposite the strainer.

4. The apparatus of claim 3 wherein the deflector is defined by a surface formed in the cap, the surface being inclined relative to the first direction of fluid flow so that fluid entering the inlet opening impinges upon the deflector.

5. The apparatus of claim 4 wherein the deflector is spaced away from the inlet opening.

6. The apparatus of claim 1 wherein the deflector is defined by a surface that is inclined to deflect the flow of fluid by about 90 degrees.

7. The apparatus of claim 1 wherein the inlet opening is located so that fluid drawn into the collector member flows toward a portion of the side wall opposite the opening, and wherein the deflector includes an inclined surface against which impinges the fluid flowing through the inlet opening so that the fluid is redirected by the deflector toward the strainer.

8. The apparatus of claim 7 wherein the surface is located away from the opening such that the path of the fluid drawn into the opening is unaffected by the deflector for a distance from the opening to a location about one-half the distance between the opening and the opposite portion of the side wall.

9. The apparatus of claim 3 further comprising alignment means for restricting attachment of the cap and the collector member to an orientation of the attached cap that locates the deflector in a position relative to the inlet opening so that the deflector directs toward the strainer fluid that is drawn into the inlet opening.

10. The apparatus of claim 1 further comprising keying means for limiting the fit between the connector and the collector member to one in which the inlet opening is aligned with the coupler, thereby to permit fluid communication between the opening and a tube that is connected to the coupler.

11. The apparatus of claim 1 wherein the deflector is constructed to include a thin wall that flexes as a solid particle carried in the fluid contacts the deflector.

12. A solids collector, comprising:
a collector member having a strainer carried on one end thereof and a cap attached to the opposing end of the collector member;
inlet means for defining a first fluid path for the inlet of fluids that carry solid particles, the fluids moving through an inlet opening in the collector member and into the collector member;
a deflector connected to extend from the cap and shaped for changing the direction of the first fluid path so that fluids that are inlet to the collector member are redirected toward the strainer; and
wherein the inlet means is formed so that the first fluid path is toward the deflector, the deflector including an inclined surface against which impinges fluid flowing through the inlet opening so that the fluid is redirected by the deflector toward the strainer.

13. The apparatus of claim 12 wherein the deflector is defined by the cap that is attached to the collector member.

14. The apparatus of claim 13 further comprising alignment means for restricting attachment of the cap and the collector member to an orientation of the attached cap that locates the deflector surface in the first fluid path.

15. The apparatus of claim 12 wherein the surface is located away from the opening by an amount such that the first fluid path direction is unchanged by the deflector for the distance of about one-half the distance across the width of the collector member.

16. The apparatus of claim 14 wherein the surface is defined by a flexible wall for absorbing energy of the inlet fluid.

17. A solids collector apparatus, comprising:
a collector member defined by a cylindrical side wall and opposing ends and having a strainer located at one of the ends so that fluid that carries solid particles may be drawn into the collector member by suction applied to the strainer end of the collector member, the collector member having an inlet opening formed in the side wall and through which opening the fluid is drawn along a first path into the collector member by the suction; and
a deflector attached to the collector member for directing toward the strainer fluid that is drawn into the inlet opening, the deflector having a first surface being inclined relative to the direction of the first fluid path so that the fluid entering the inlet opening impinges upon the deflector; and
the deflector including a second surface adjacent to the first surface and inclined to provide a surface against which fluid drawn into the collector member through a second fluid path may be directed toward the strainer.

18. The apparatus of claim 17 further comprising connector means for coupling to the collector member a pair of tubular elements for defining the first and second fluid paths.

19. A collector member, comprising:
a hollow body having a cylindrical side wall and opposing ends, one end of the body having openings formed therein for defining a strainer, the other end of the body defining an upper edge;
the body defining an inlet opening extending through the side wall and located between the upper edge and the strainer; and
at least one key formed in and protruding from the side wall.

20. The collector member of claim 19 wherein the body further defines two holes in the side wall, each hole being opposite the other hole and located proximal to the edge of the body.

21. A collector member, comprising:
a hollow body having a cylindrical side wall and opposing ends, one end of the body having openings formed therein for defining a strainer, the other end of the body defining an upper edge;
the body defining an inlet opening extending through the side wall and located between the upper edge and the strainer; and
cap securing means defined in the body for receiving a cap that has two bosses protruding therefrom.

22. The collector member of claim 21 wherein the cap securing means includes two holes defined in the side wall of the body, each being opposite the other hole and located proximal to the edge of the body.

23. The collector member of claim 22 wherein one of the two holes is larger than the other.

24. The collector member of claim 21 further comprising two slits formed through the body side wall, each slit extending between a hole and the edge of the body.

25. The collector member of claim 21 further comprising at least one key formed by the side wall, the key comprising a protrusion extending from the remaining portion of the side wall.

* * * * *